(12) United States Patent
Ma et al.

(10) Patent No.: US 12,275,750 B2
(45) Date of Patent: Apr. 15, 2025

(54) 1,2-BIS(DIPHENYLPHOSPHINOALKY-LAMIDO)-1,2-DISUBSTITUTED ETHANE, AND ITS SYNTHESIS AND APPLICATION

(71) Applicant: ZHEJIANG UNIVERSITY, Zhejiang (CN)

(72) Inventors: Shengming Ma, Zhejiang (CN); Yuchen Zhang, Zhejiang (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 423 days.

(21) Appl. No.: 17/629,075

(22) PCT Filed: Jul. 8, 2020

(86) PCT No.: PCT/CN2020/100786
§ 371 (c)(1),
(2) Date: Jan. 21, 2022

(87) PCT Pub. No.: WO2021/012949
PCT Pub. Date: Jan. 28, 2021

(65) Prior Publication Data
US 2022/0242892 A1    Aug. 4, 2022

(30) Foreign Application Priority Data
Jul. 22, 2019   (CN) .......................... 201910660633.8

(51) Int. Cl.
*C07F 9/50*    (2006.01)
*C07D 231/26*  (2006.01)

(52) U.S. Cl.
CPC .......... *C07F 9/5027* (2013.01); *C07D 231/26* (2013.01)

(58) Field of Classification Search
CPC ........................... C07F 9/5027; C07D 231/26
See application file for complete search history.

(56) References Cited

FOREIGN PATENT DOCUMENTS

WO    WO-2019243580 A1  *  12/2019  ............. C08K 5/101

OTHER PUBLICATIONS

Shixiong et al., Acta Chimica Sinica, 2014, vol. 7, Issue 7, 825-829 (Year: 2014).*
Organocatalyzed Asymmetric Allylic Alkylation of MDB-Carbonates with Pyrazolonesâ (Shixiong et al, Acta Chimica Sinica, 2014, vol. 7, Issue 7, 825-829) (Year: 2014).*
Gomes et al., "N-heteroatom substitution effect in 3-aza-cope rearrangements," Chemistry Central Journal, vol. 7, No. 94, 2013, pp. 1-12.
Ito et al., "Coordination Behavior of N,N'-Bis(diisopropylphosphinoacetyl)-o-phenylenediamide with Ni" and Cu' Ions, European Journal of Inorganic Chemistry, 2017, pp. 3498-3507.
Lange et al., "Dendrimer—Based Multinuclear Gold(I) Complexes," Inorganic Chemistry, vol. 35, No. 3., 1996, pp. 637-642.
Li et al., "Synthesis and crystal structures of copper(1) Iodide complexes chelating with bis(ethylamidophosphine)," Inorganic Chemistry Communications, vol. 6, 2003 (Published online Oct. 7, 2003), pp. 1451-1453.
Lin et al., "Highly Enantioselective Allylic C—H Alkylation of Terminal Olefins with Pyrazol-5-ones Enabled by Cooperative Catalysis of Palladium Complex and Bronsted Acid," Journal of the American Chemical Society, Oct. 9, 2016, pp. 14354-14361.
Wu et al., "DABCO—mediated one-pot sequential transformation: convenient access to fluorinated 1H-pyrazol-5(4H)-ones," Tetrahedron Letters, vol. 53, 2012 (Available online Jun. 29, 2012), pp. 4828-4831.

* cited by examiner

*Primary Examiner* — Noble E Jarrell
*Assistant Examiner* — Phillip Matthew Rzeczycki
(74) *Attorney, Agent, or Firm* — Birch, Stewart, Kolasch & Birch, LLP

(57) ABSTRACT

The present invention relates to the design and synthesis of a class of novel chiral phosphine ligand, 1,2-bis(diphenylphosphinoalkylamido)-1,2-disubstituted ethane, and use in asymmetric catalytic reactions, such as asymmetric catalytic synthesis of pyrazoline-5-one with a chiral quaternary carbon center, i.e., highly enantioselective synthesis of 3-methyl-4-benzyl-4-(2-butyl-2,3-butadienyl)pyrazoline-5-one by using 3-methyl-4-benzylpyrazoline-5-one and benzyl (2-butyl-2,3-butadienyl) carbonate with tris(dibenzylideneacetone)dipalladium-chloroform adduct and this novel ligand as catalysts. The ligand designed by this present invention has the following advantages: the structure is novel, the synthesis and enlarge are simple, the enantioselective control effect in the practical reaction is excellent, which has a broad application prospect in chiral catalysis.

10 Claims, No Drawings

1,2-BIS(DIPHENYLPHOSPHINOALKYLAMIDO)-1,2-DISUBSTITUTED ETHANE, AND ITS SYNTHESIS AND APPLICATION

TECHNICAL FIELD

The present invention belongs to the field of chemical synthesis, and relates to a class of new chiral phosphine ligand 1,2-bis(diphenylphosphinoalkylamido)-1,2-disubstituted ethane, and its synthesis and application.

BACKGROUND OF THE INVENTION

In recent years, a series of ligands such as Trost ligand, which control enantioselectivity by constructing "chiral pockets", have been widely used in asymmetric allylation reactions. However, Trost ligands show poor control of enantioselectivity and diastereoselectivity in asymmetric allylation reactions via allyl metal intermediates. This shows that there is room for improvement and redesign of this class of ligand. In Trost ligand, benzene or naphthalene ring is used as the bridge connecting the chiral center and phosphine, which has certain rigidity in structure. Therefore, the present invention designs the structure of Trost ligand with flexibility, and proves that "to overcome rigidity with softness" is effective in practical application examples. The design and application of new ligand are the complement and perfection of this control model ligand system.

SUMMARY OF THE INVENTION

Aiming at the defect of the existing ligand, the present invention provides a class of novel chiral phosphine ligand 1,2-bis(diphenylphosphinoalkylamido)-1,2-disubstituted ethane and its preparation method, as well as the highly enantioselective synthesis of chiral 3-methyl-4-benzyl-4-(2-butyl-2,3-butadienyl)pyrazoline-5-one with the above ligand and palladium as catalysts.

The present invention provides a class of new chiral phosphine ligand, 1,2-bis(diphenylphosphinoalkylamido)-1,2-disubstituted ethane, which has the following structure:

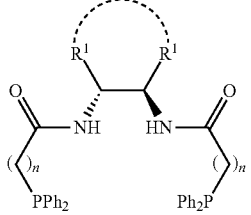

formula (I)

In the said formula (I),
$R^1$=—$(CH_2)_3$—, —$(CH_2)_4$—, phenyl group, phenyl group substituted by C1-C10 alkyl, phenyl group substituted by halogen, α-naphthyl group; n=1-6;
preferably,
$R^1$=—$(CH_2)_4$—, phenyl group; n=1-3.

The present invention also provides a preparation method for the phosphine ligand shown in formula (I), which uses diphenylphosphinoalkyl carboxylic acid (or its N-hydroxysuccinimide ester) and chiral diamine as raw materials to obtain a chiral phosphine ligand through a simple amidation reaction.

The said method comprises the following steps:
Method 1:

In an organic solvent, the said chiral phosphonic ligand can be obtained by using 1,2-disubstituted-1,2-diaminoethane, diphenylphosphinoacetic acid, p-dimethylaminopyridine and 1-ethyl-(3-dimethylaminopropyl)carbodiimide hydrochloride as reaction raw materials through amidation reaction, which has the following reaction equation:

reaction equation (a)

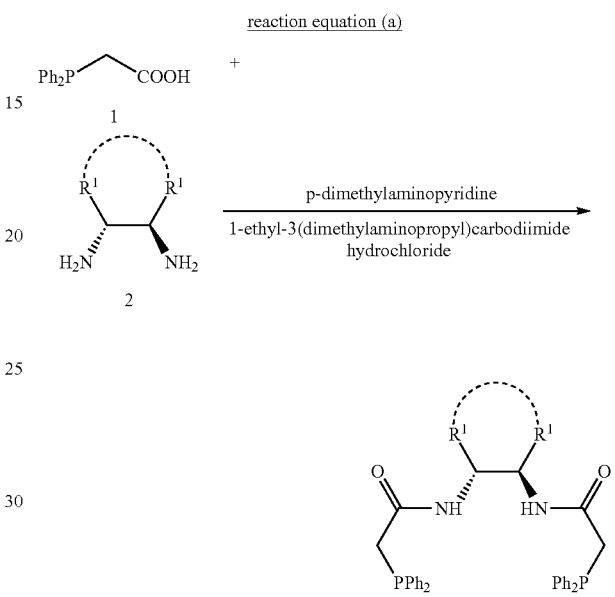

Wherein,
$R^1$=—$(CH_2)_3$—, —$(CH_2)_4$—, phenyl group, phenyl group substituted by C1-C10 alkyl, phenyl group substituted by halogen, α-naphthyl group;
Preferably,
$R^1$=—$(CH_2)_4$—, phenyl group.

Wherein, the said organic solvent is methylene chloride.

Wherein, the said amidation reaction temperature is 20-30° C.; preferably, is room temperature.

Wherein, the said amidation reaction time is 10-24 hours; preferably, is 10 hours.

Wherein, the molar ratio of the said diphenylphosphinoacetic acid, 1,2-disubstituted-1,2-diaminoethane, p-dimethylaminopyridine and 1-ethyl-(3-dimethylaminopropyl)carbodiimide hydrochloride is (2.1-2.2):1.0:2.1:2.2; preferably, is 2.1:1.0:2.1:2.2.

The present invention also provides post-treatment steps: transferring the reaction liquid to a separatory funnel, washing three times with water twice the amount of organic solvent, drying the organic phase with anhydrous sodium sulfate, filtering, concentrating, and subjecting to fast column chromatography to obtain the said ligand.

Method 2:

In an organic solvent, the said chiral phosphine ligand can be obtained by using N-hydroxysuccinimide diphenylphosphonyl alkyl acid ester and 1,2-disubstituted-1,2-diaminoethane as reaction raw materials through amidation reaction which has the following reaction equation:

reaction equation (b)

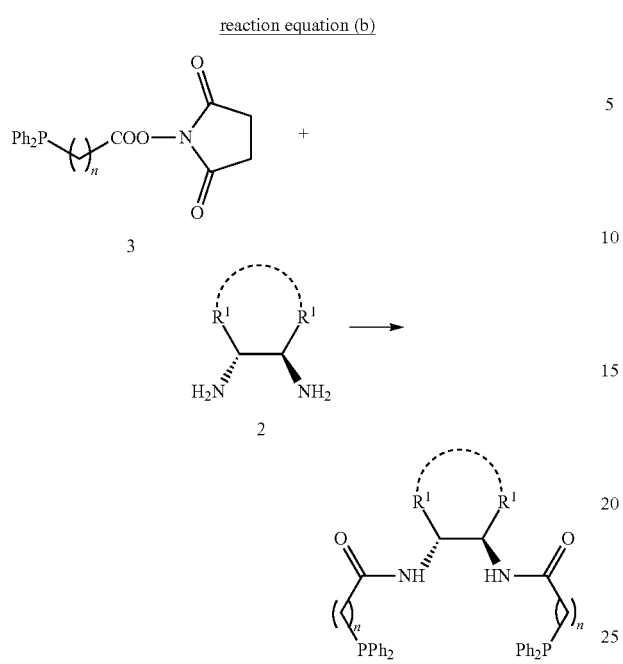

In reaction equation (b),
$R^1$=—$(CH_2)_3$—, —$(CH_2)_4$—, phenyl group, phenyl group substituted by C1-C10 alkyl, phenyl group substituted by halogen, α-naphthyl group; n=1-6;
preferably,
$R^1$=—$(CH_2)_4$—, phenyl group; n=1-3.

Wherein, the said organic solvent is methylene chloride.

Wherein, the said amidation reaction temperature is 20-30° C.; preferably, is room temperature.

Wherein, the said amidation reaction time is 10-20 hours; preferably, is 10 hours.

Wherein, the molar ratio of the said diphenylphosphinoalkyl acid N-hydroxysuccinimide ester and 1,2-disubstituted-1,2-diaminoethane is (2.1-2.2):1.0; preferably, is 2.2:1.0.

The present invention also provides post-treatment steps: quenching the reaction with water, transferring to a separatory funnel, separating the liquids, extracting the aqueous layers with dichloromethane, drying the organic layers with anhydrous sodium sulfate, filtering, concentrating, and subjecting to fast column chromatography to obtain the said liagand.

The present invention also provides a method for infiltrating glassy the said chiral phosphine ligand with ethyl acetate to precipitate into a white solid.

In a specific embodiment, the said chiral phosphine ligand 1,2-bis(diphenylphosphinoalkylamido)-1,2-disubstituted ethane is prepared as follows:

One has the following reaction equation:

reaction equation (a')

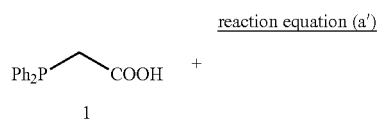

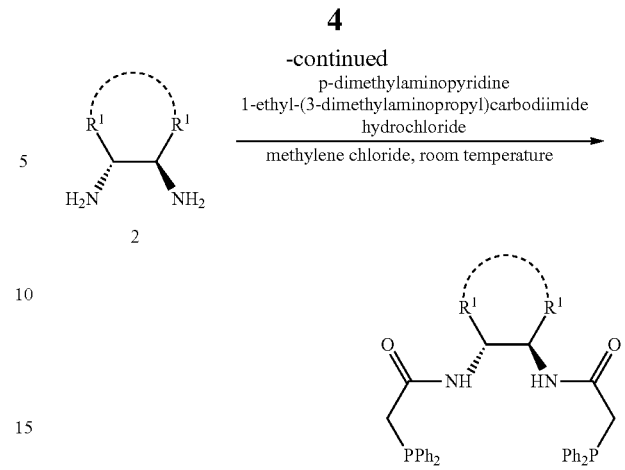

In reaction equation (a'),
$R^1$=—$(CH_2)_3$—, —$(CH_2)_4$—, phenyl group, phenyl group substituted by C1-C10 alkyl, phenyl group substituted by halogen, α-naphthyl group; preferably, $R^1$=—$(CH_2)_3$—, —$(CH_2)_4$—, phenyl group.

The reaction comprises the following steps:
(1) Adding 1,2-disubstituted-1,2-diaminoethane and dichloromethane into a three-necked flask, then adding dichloromethane solution of diphenylphosphinoacetic acid, p-dimethylaminopyridine and the dichloromethane solution of 1-ethyl-(3-dimethylaminopropyl)carbodiimide hydrochloride, and stirring at room temperature for 10 hours;
(2) Transferring reaction solution to a separatory funnel, washing with water twice the amount of the solvent for three times, drying the organic layers with anhydrous sodium sulfate, filtering, concentrating, and subjecting to fast column chromatography to obtain the ligand.

The other one has a following reaction equation:

reaction equation (b')

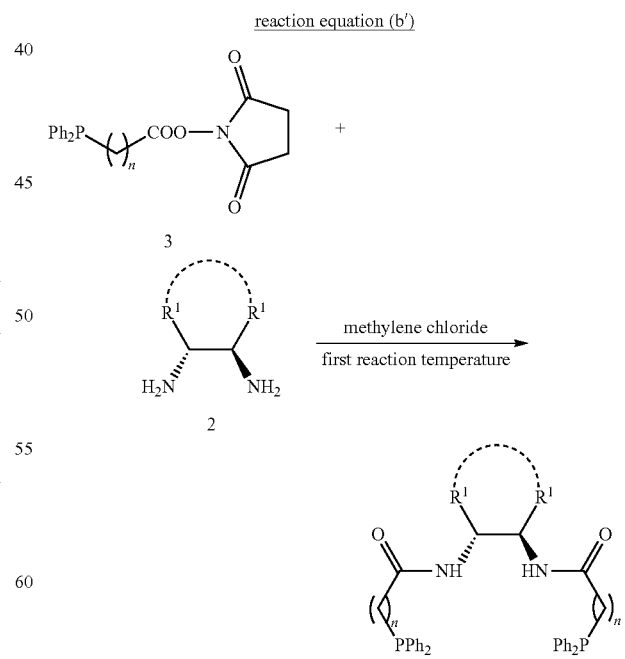

In reaction equation (b'),
$R^1$=—$(CH_2)_3$—, —$(CH_2)_4$—, phenyl group, phenyl group substituted by C1-C10 alkyl, phenyl group substituted by halogen, α-naphthyl group; n=1-6; preferably, $R^1$=—$(CH_2)_3$—, —$(CH_2)_4$—, phenyl group; n=1-3.

The reaction comprises the following steps:
(1) Adding diphenylphosphinoalkyl acid N-hydroxysuccinimide ester and dichloromethane into the reaction tube, then adding 1,2-disubstituted-1,2-diaminoethane and dichloromethane, and stirring at the first reaction temperature for 10-20 hours;
(2) Quenching reaction with water, transferring to the separatory funnel, separating the liquids, extracting the aqueous layers with dichloromethane, drying the organic layers with anhydrous sodium sulfate, filtering, concentrating, subjecting to fast column chromatography to obtain ligand.

The first reaction temperature of the present invention is 20-30° C.

The molar ratio of compound 1 and compound 2 is 2.1:1.0; the molar ratio of compound 3 and compound 2 is 2.2:1.0.

The present invention also provides the use of the said 1,2-bis(diphenylphosphinoalkylamido)-1,2-disubstituted ethane in the highly enantioselective preparation of chiral 3-methyl-4-benzyl-4-(2-butyl-2,3-butadienyl)pyrazoline-5-one, wherein, the said preparation method of the chiral 3-methyl-4-benzyl-4-(2-butyl-2,3-butadienyl)pyrazoline-5-one comprising the following steps: in an organic solvent, using tris(dibenzylideneacetone)dipalladium-chloroform adduct, 1,2-bis(diphenylphosphinoalkylamido)-1,2-disubstituted ethane, benzyl(2-alkyl-2,3-butadienyl) carbonate and 3-methyl-4-benzyl-pyrazoline-5-one as reaction raw materials to obtain the said chiral 3-methyl-4-benzyl-4-(2-butyl-2,3-butadienyl)pyrazoline-5-one, which has the following reaction equation:

reaction equation (c)

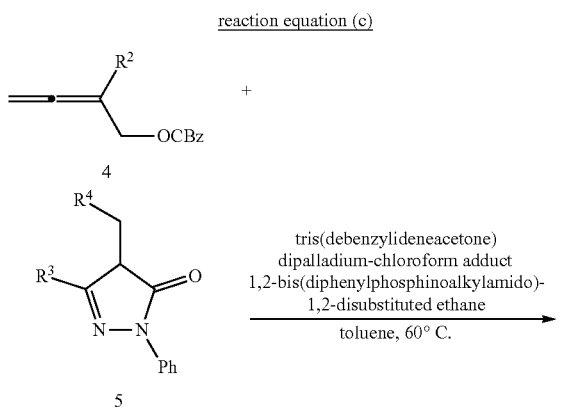

In reaction equation (c),
$R^2$ is C1-C10 alkyl group; $R^3$ is C1-C10 alkyl group; $R^4$ is phenyl group substituted by halogen, phenyl group substituted by C1-C10 alkyl group, benzyl group, α-naphthyl group, C1-C10 alkyl group, alkenyl group.

Preferably, $R^2$ is methyl group, n-butyl group, n-octylc group, etc.; $R^3$ is methyl group; $R^4$ is phenyl group substituted by chlorine, phenyl group substituted by methyl group, benzyl group, α-naphthyl group, methyl group, vinyl group.

Wherein, the said organic solvent is one or more of toluene, trichloromethane, dichloromethane, etc.; preferably, is toluene.

Wherein, the said reaction temperature is 30-60° C.; preferably, is 60° C.

Wherein, the said reaction time is 8-24 hours; preferably, is 12-13 hours.

Wherein, the molar ratio of the said benzyl (2-alkyl-2,3-butadienyl) carbonate and 3-methyl-4-benzyl-pyrazoline-5-one is 1.0:(1.0-1.6); preferably, is 1.0:1.2 or 1.0:1.4.

Wherein, the molar ratio of the said benzyl (2-alkyl-2,3-butadienyl) carbonate and the organic solvent is 0.02-0.1 mmol/mL; preferably, is 0.02 mmol/mL.

In a specific embodiment, the said chiral 3-methyl-4-benzyl-4-(2-butyl-2,3-butadienyl)pyrazoline-5-one is prepared as follows:

reaction equation (c')

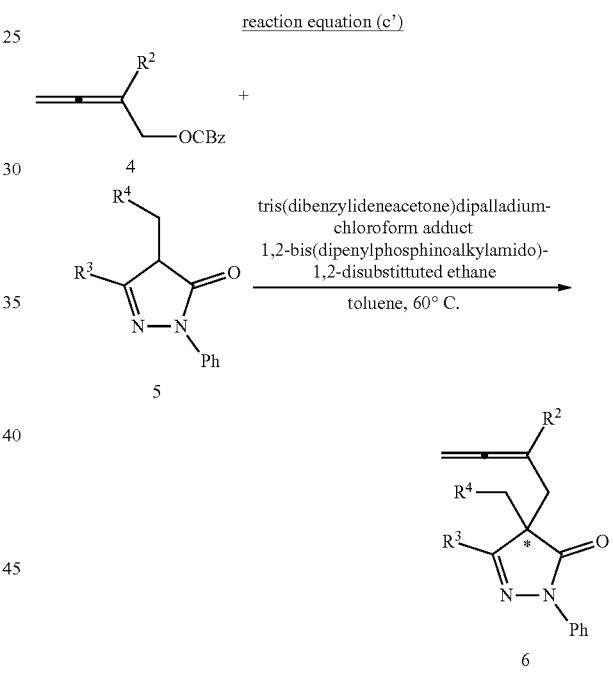

In reaction equation (c'),
$R^2$ is C1-C10 alkyl group; $R^3$ is C1-C10 alkyl group; $R^4$ is phenyl group substituted by halogen, phenyl group substituted by C1-C10 alkyl group, benzyl group, α-naphthyl group, C1-C10 alkyl group, alkenyl group.

Preferably, $R^2$ is methyl group, n-butyl group, n-octylc group, etc.; $R^3$ is methyl group; $R^4$ is phenyl group substituted by chlorine, phenyl group substituted by methyl group, benzyl group, α-naphthyl group, methyl group, vinyl group.

The reaction comprises the following steps:
(1) Adding tris(dibenzylideneacetone)dipalladium-chloroform adduct, 1,2-bis(diphenylphosphinoalkylamido)-1,2-disubstituted ethane and toluene into the reaction tube, then adding benzyl (2-alkyl-2,3-butadienyl) carbonate and toluene, 3-methyl-4-benzyl-pyrazoline-5-one and toluene, and stirring at 60° C. for 12-13 hours;

(2) Concentrating and subjecting to fast column chromatography to obtain 3-methyl-4-benzyl-4-(2-alkyl-2,3-butadienyl)pyrazoline-5-one.

The present invention uses toluene as the organic solvent for synthesis of 3-methyl-4-benzyl-4-(2-alkyl-2,3-butadienyl)pyrazoline-5-one. The molar ratio of compound 4 and compound 5 is 1.0:1.2 or 1.0:1.4.

The molar ratio of compound 4 and toluene is 0.05 mmol/mL.

The present invention also provides a class of chiral 3-methyl-4-benzyl-4-(2-alkyl-2,3-butadienyl)pyrazoline-5-one compounds, which has the following structural formula:

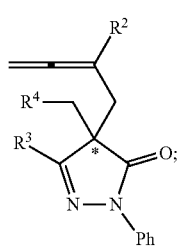

formula (6)

Wherein, $R^2$ is C1-C10 alkyl group; $R^3$ is C1-C10 alkyl group; $R^4$ is phenyl group substituted by halogen, phenyl group substituted by C1-C10 alkyl group, benzyl group, α-naphthyl group, C1-C10 alkyl group, alkenyl group.

Preferably, $R^2$ is methyl group, n-butyl group, n-octylc group, etc.; $R^3$ is methyl group; $R^4$ is phenyl group substituted by chlorine, phenyl group substituted by methyl group, benzyl group, α-naphthyl group, methyl group, vinyl group.

The present invention relates to a new class of ligand and its use to the highly enantioselective synthesis of 3-methyl-4-benzyl-4-(2-alkyl-2,3-butadienyl)pyrazoline-5-one by using 3-methyl-4-benzylpyrazoline-5-one and benzyl (2-alkyl-2,3-butadienyl) carbonate as raw meaterials with tris(dibenzylideneacetone)dipalladium-chloroform adduct and this ligand as catalysts, The method for ligand synthesis is easy to operate, readily accessible to the raw materials and reagents, and in good control of the reaction enantioselectivity in practical use.

The present invention is a further improvement of the structure of traditional Trost ligand and makes up for the defects of enantioselective control of Trost ligand in some reactions.

The present invention is innovative in developing a series of novel and practical chiral ligands.

The present invention has the beneficial effect that the ligand designed by the present invention has novel structure, is easy to synthesize and enlarge, and has excellent enantioselective control effect when used in the actual reaction, which has a broad application prospect in chiral catalysis.

PREFERRED EMBODIMENTS OF THE INVENTION

The following examples and reaction equation are given for further illustrating the specific solutions of the present invention. The protection of the invention is not limited to the following embodiments. Without departing from the spirit and scope of the idea of the invention, all changes and advantages that can be thought of by a person skilled in the field are included in the present invention and are protected by the attached claims. The process, conditions, reagents and experimental methods of the implementation of the present invention are all general knowledge and common knowledge in the field except for the contents specially mentioned below, and the present invention has no special limitation. The following examples are given for the further understanding of the present invention and are not intended to limit the present invention.

Note: in the equation of the following examples, "equiv" refers to equivalent; "mmol" refers to millmole, "EDCI" refers to 1-ethyl-(3-dimethylaminopropyl)carbodiimide hydrochloride; "DMAP" refers to p-dimethylaminopyridine; "DCM" refers to dichloromethane; "rt" refers to room temperature; "Pd$_2$(dba)$_3$·CHCl$_3$" refers to tris(dibenzylideneacetone)dipalladium-chloroform adduct; "(R,R)-L1" refers to the ligand synthesized in Example (1); "N$_2$" refers to nitrogen; "toluene" refers to toluene.

Example (1) (1R,2R)-1,2-bis(diphenylphosphinoacetamido) cyclohexane ((R,R)-L1) (zyc-4-7)

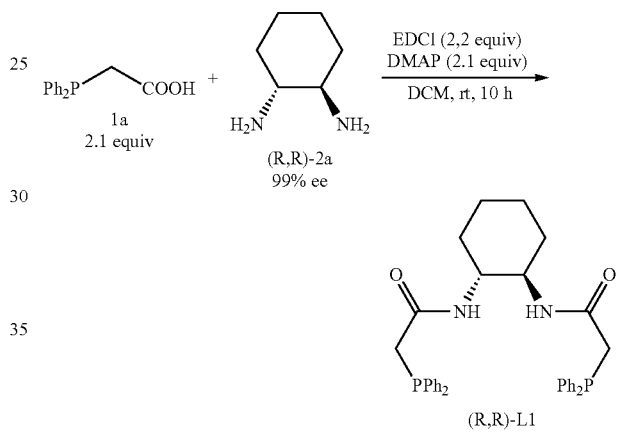

(R,R)-1,2-cyclohexanediamine (846.0 mg, 7.41 mmol, 99% ee) and dichloromethane (10 mL), diphenylphosphinoacetic acid (3800.0 mg, 15.56 mmol) and dichloromethane (20 mL), and p-dimethylaminopyridine (1899.4 mg, 15.56 mmol) were added to a dried three-necked flask. Then 1-ethyl-(3-dimethylaminopropyl)carbodiimide hydrochloride (3125.5 mg, 16.30 mmol) dissolved in 20 mL dichloromethane was dropped into the three-necked flask, stirred for 10 hours at room temperature, transferred to a separatory funnel and washed with water (100 mL×3). The combined organic phase was dried over anhydrous sodium sulfate. After filtration and evaporation of the solvent, the crude residual was purified by chromatography on silica gel (dichloromethane/methanol=1000/1 (150 mL) to 100/1 (1000 mL)) to afford the product (R,R)-L1 (1718.7 mg, 41%) as a solid.

(R,R)-L1: melting point: 217.4-218.0° C. (dichloromethane/n-hexane). [α]$_D^{20}$=+32.9 (c=0.995, CHCl$_3$); $^1$H NMR (300 MHz, CDCl$_3$) δ 7.61-7.11 (m, 20H, ArH), 5.99 (d, J=3.9 Hz, 2H, NH×2), 3.62-3.36 (m, 2H, NCH×2), 3.01-2.68 (m, 4H, CH$_2$×2), 1.86-1.50 (m, 4H, CH$_2$×2), 1.33-1.06 (m, 2H, CH$_2$), 1.06-0.80 (m, 2H, CH$_2$); $^{13}$C NMR (75 MHz, CDCl$_3$) δ 169.9 (d, J=8.3 Hz), 137.5 (d, J=13.8 Hz), 137.3 (d, J=13.8 Hz), 133.0, 132.7, 132.5, 132.3, 129.1, 128.8, 128.6, 128.54, 128.50, 128.46, 53.6, 37.4 (d, J=20.7 Hz), 32.0, 24.5;

$^{31}$P NMR (121.5 MHz, CDCl$_3$) δ-16.8; IR (KBr) v (cm$^{-1}$) 3292, 3067, 3052, 2933, 2912, 2854, 1627, 1530, 1480, 1433, 1401, 1328, 1147; MS (EI): m/z (%) 566 ([M]$^+$, 29.26), 381 (100); Anal. Calcd. for C$_{34}$H$_{36}$N$_2$O$_2$P$_2$ (%): C 72.07, H 6.40, N 4.94; Found: C 72.01, H 6.42, N 4.76.

Example (2) (1S,2S)-1,2-bis(diphenylphosphinoacetamido)cyclohexane (S,S)-(L1) (zyc-4-52)

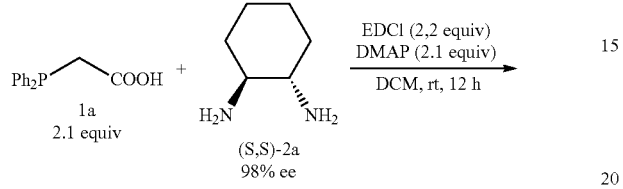

Example (3) (1R,2R)-1,2-bis(diphenylphosphinopropionamido)cyclohexane (R,R)-(L2) (zyc-3-118, 186)

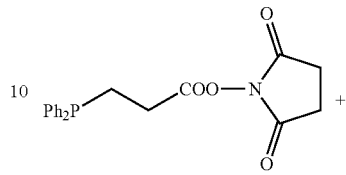

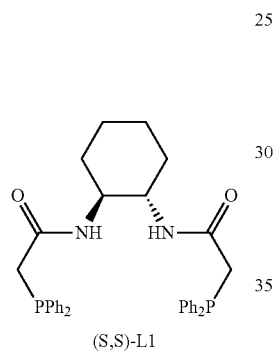

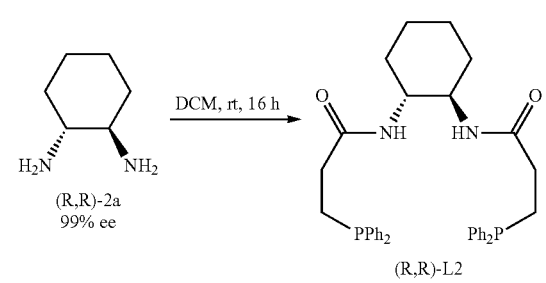

Operations were conducted by referring to Example (1). (S,S)-1,2-cyclohexanediamine (764.1 mg, 6.70 mmol, 98% ee)/dichloromethane (10 mL), diphenylphosphinoacetic acid (3451.7 mg, 14.10 mmol)/dichloromethane (20 mL), p-dimethylaminopyridine (1723.0 mg, 14.10 mmol), and 1-ethyl-(3-dimethylaminopropyl)carbodiimide hydrochloride (2826.6 mg, 14.74 mmol)/dichloromethane (20 mL) were added to a dried three-necked flask and stirred for 12 hours at room temperature to obtain (S,S)-L1 (1252.3 mg, 33%) (dichloromethane/methanol=1000/1 (300 mL) to 100/1 (800 mL)) as a solid.

(S,S)-L1: melting point: 216.9-217.9° C. (dichloromethane/n-hexane). [α]$_D^{20}$=-33.3 (c=0.990, CHCl$_3$); $^1$H NMR (300 MHz, CDCl$_3$) δ 7.53-7.20 (m, 20H, ArH), 5.99 (d, J=5.1 Hz, 2H, NH×2), 3.59-3.40 (m, 2H, NCH×2), 2.96-2.77 (m, 4H, PCH$_2$×2), 1.86-1.70 (m, 2H, CH$_2$), 1.70-1.54 (m, 2H, CH$_2$), 1.28-1.08 (m, 2H, CH$_2$), 1.06-0.84 (m, 2H, CH$_2$); $^{13}$C NMR (75 MHz, CDCl$_3$) δ 170.0 (d, J=8.3 Hz), 137.5 (d, J=13.1 Hz), 137.3 (d, J=14.5 Hz), 133.0, 132.7, 132.5, 132.3, 129.1, 128.8, 128.6, 128.55, 128.51, 128.47, 53.6, 37.4 (d, J=20.7 Hz), 32.0, 24.5; $^{31}$P NMR (121.5 MHz, CDCl$_3$) δ-16.8; IR (KBr) v (cm$^{-1}$) 3292, 3067, 3051, 2931, 2854, 1628, 1529, 1481, 1433, 1399, 1327, 1190, 1143; MS (EI): m/z (%) 566 ([M]$^+$, 32.57), 381 (100); Anal. Calcd. for C$_{34}$H$_{36}$N$_2$O$_2$P$_2$ (%): C 72.07, H 6.40, N 4.94; Found: C 72.03, H 6.44, N 4.81.

Compounds 3a (1564.1 mg, 4.4 mmol) and dichloromethane (4 mL), (R,R)-1,2-cyclohexanediamine (228.6 mg, 2.0 mmol, 99% ee) and dichloromethane (2 mL) were added to a dried reaction tube, then stirred for 16 hours at room temperature. Then 10 mL of water was added to quench the reaction, transferred to the separatory funnel, and extracted with dichloromethane (10 mL×3). The combined organic phase was dried over anhydrous sodium sulfate. After filtration and evaporation of the solvent, the crude residual was purified by chromatography on silica gel (dichloromethane/methanol=100/0 (300 mL) to 100/1 (500 mL) to afford a solid. The resulting solid was recrystallized from ethyl acetate and collected by suction filtration washed with ethyl acetate to afford the product (R,R)-L2 (852.6 mg, 72%) as a solid.

(R,R)-L2: melting point: 152.4-153.2° C. (ethyl acetate). [α]$_D^{20}$=+0.3 (c=1.045, CHCl$_3$); $^1$H NMR (300 MHz, CDCl$_3$) δ 7.46-7.32 (m, 8H, ArH), 7.32-7.22 (m, 12H, ArH), 6.11 (d, J=6.9 Hz, 2H, NH×2), 3.68-3.51 (m, 2H, NCH×2), 2.37-2.10 (m, 8H, CH$_2$×4), 2.03-1.90 (m, 2H, CH$_2$), 1.78-1.62 (m, 2H, CH$_2$), 1.37-1.08 (m, 4H, CH$_2$×2); $^{13}$C NMR (75 MHz, CDCl$_3$) δ 172.7 (d, J=13.1 Hz), 137.8 (d, J=3.5 Hz), 137.6 (d, J=3.5 Hz), 132.7, 132.6, 132.5, 132.4, 128.61, 128.58, 128.4, 128.3, 53.6, 32.7 (d, J=18.6 Hz), 32.0, 24.5, 23.3 (d, J=12.5 Hz); $^{31}$P NMR (121.5 MHz, CDCl$_3$) δ-15.9; IR (KBr) v (cm$^{-1}$) 3273, 3069, 2933, 2855, 1639, 1546, 1476, 1433, 1257; MS (EI): m/z (%) 594 ([M]$^+$, 11.45), 256 (100); HRMS calcd. for C$_{36}$H$_{40}$N$_2$O$_2$P$_2$ [M$^+$]: 594.2565; Found: 594.2563.

Example (4) (1R,2R)-1,2-bis(diphenylphosphinobutyramido)cyclohexane (R,R)-(L3) (zyc-3-198)

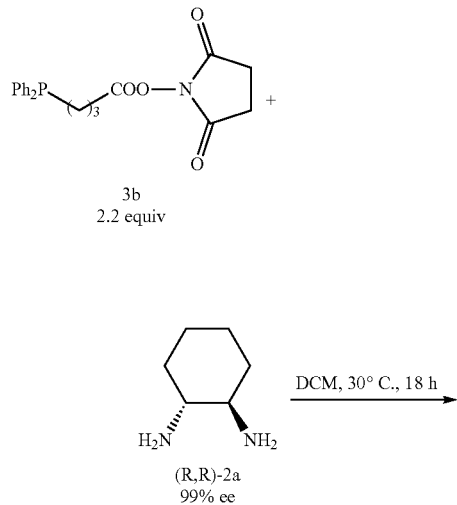

Compound 3b (890.5 mg, 2.2 mmol) and dichloromethane (2 mL), (R,R)-1,2-cyclohexanediamine (117.1 mg, 1.0 mmol, 99% ee) and dichloromethane (1 mL) were added to a dried reaction tube, then stirred at 30° C. for 18 hours. 5 mL water was added to quench the reaction, transferred to separatory funnel, and extracted with dichloromethane (10 mL×3). The combined organic phase was dried over anhydrous sodium sulfate. After filtration and evaporation of the solvent, the crude residual was purified by chromatography on silica gel (dichloromethane/methanol=100/0 (300 mL) to 100/1 (600 mL), and then recrystallized with dichloromethane/n-hexane system to afford the product (R,R)-L3 (344.8 mg, 54%) as a solid.

(R,R)-L3: melting point: 166.8-167.6° C.(dichloromethane/n-hexane). $[\alpha]_D^{20}$=+22.4 (c=1.000, CHCl$_3$); $^1$H NMR (300 MHz, CDCl$_3$) δ 7.55-7.09 (m, 20H, ArH), 6.03 (d, J=4.5 Hz, 2H, NH×2), 3.72-3.53 (m, 2H, NCH×2), 2.28-2.06 (m, 4H, CH$_2$×2), 2.06-1.88 (m, 6H, CH$_2$×3), 1.84-1.59 (m, 6H, CH$_2$×3), 1.38-1.08 (m, 4H, CH$_2$×2); $^{13}$C NMR (75 MHz, CDCl$_3$) δ 172.9, 138.4 (d, J=2.8 Hz), 138.2 (d, J=3.5 Hz), 132.7, 132.5, 128.5, 128.4, 128.3, 53.6, 37.5 (d, J=13.1 Hz), 32.2, 27.4 (d, J=11.8 Hz), 24.6, 22.1 (d, J=17.9 Hz); $^{31}$P NMR (121.5 MHz, CDCl$_3$) δ-17.2; IR (KBr) v (cm$^{-1}$) 3344, 3068, 3045, 2943, 2854, 1636, 1521, 1478, 1432, 1409, 1375; MS (EI): m/z (%) 622 ([M]$^+$, 47.62), 270 (100); Anal. Calcd. for C$_{38}$H$_{44}$N$_2$O$_2$P$_2$ (%): C 73.29, H 7.12, N 4.50; Found: C 73.11, H 7.13, N 4.30.

Example (5) (1R,2R)-1,2-diphenyl-1,2-bis(diphenylphosphinopropionamido)ethane (R,R)-(L4) (zyc-3-181)

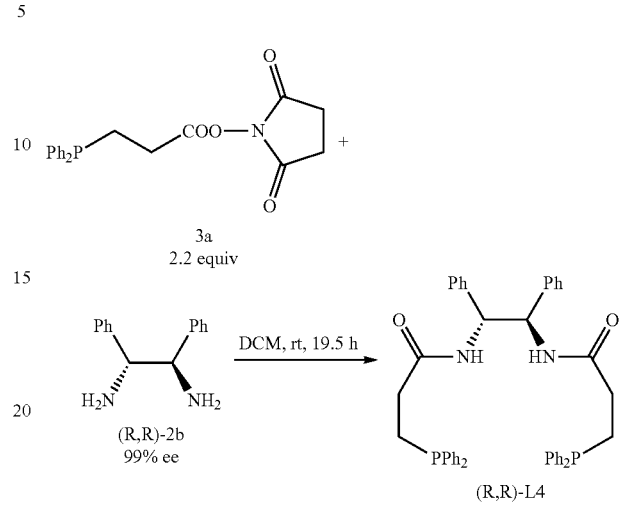

(R,R)-1,2-diphenyl 1,2-ethylenediamine (212.6 mg, 1.0 mmol, 99% ee), compound 3a (781.9 mg, 2.2 mmol) and dichloromethane (8 mL) were added to a dried reaction tube, then stirred for 19.5 hours in room temperature. 10 mL of water was added to quench the reaction, transferred to a separatory funnel, extracted with dichloromethane (10 mL×3). The combined organic phase was dried over anhydrous sodium sulfate. After filtration and evaporation of the solvent, the crude residual was purified by chromatography on silica gel (dichloromethane/methanol=100/0 (500 mL) to 100/1 (600 mL)) to afford a solid. The resulting solid was recrystallized from ethyl acetate and collected by suction filtration washed with ethyl acetate to afford the product (R,R)-L4 (561.3 mg, 79%, purity=98%) as a solid.

(R,R)-L4: melting point: 140.8-141.9° C. (ethyl acetate). $[\alpha]_D^{20}$=−64.5 (c=1.050, CHCl$_3$); $^1$H NMR (300 MHz, CDCl$_3$) δ 7.44-7.22 (m, 20H, ArH), 7.20-7.11 (m, 6H, ArH), 7.11-7.01 (m, 4H, ArH), 6.76-6.62 (m, 2H, NH×2), 5.28-5.16 (m, 2H, NCH×2), 2.36-2.13 (m, 8H, CH$_2$×4); $^{13}$C NMR (75 MHz, CDCl$_3$) δ 173.0 (d, J=13.1 Hz), 138.5, 137.8, 137.6 (d, J=1.4 Hz), 132.8, 132.7, 132.6, 132.5, 128.8, 128.7, 128.6, 128.5, 127.8, 127.5, 59.4, 32.7 (d, J=17.9 Hz), 23.2 (d, J=12.4 Hz); $^{31}$P NMR (121.5 MHz, CDCl$_3$) δ-16.1; IR (KBr) v (cm$^{-1}$) 3287, 3068, 3028, 2929, 1644, 1535, 1493, 1476, 1433, 1364, 1248; MS (EI): m/z (%) 692 ([M]f, 5.29), 346 (100); HRMS calcd. for C$_{44}$H$_{42}$N$_2$O$_2$P$_2$ [M$^+$]: 692.2722; Found: 692.2722.

Example (6) (1S,2S)-1,2-diphenyl-1,2-bis(diphenylphosphinopropionamido)ethane (S,S)-(L4) (zyc-4-15)

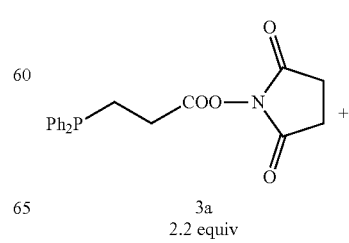

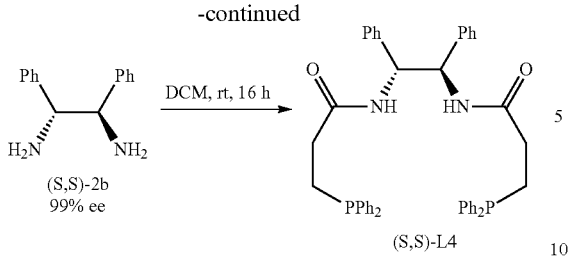

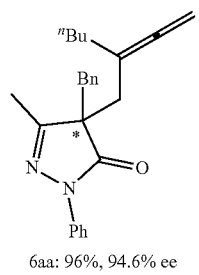

6aa: 96%, 94.6% ee (S,S)-1,2-diphenyl 1,2-ethylenediamine (212.5 mg, 1.0 mmol, 99% ee), compound 3a (782.3 mg, 2.2 mmol) and dichloromethane (8 mL) were added to a dried reaction tube, then stirred for 16 hours at room temperature. 10 mL water was added to quench the reaction, transferred to separatory funnel, extracted with dichloromethane (10 mL×3). The combined organic phase was dried over anhydrous sodium sulfate. After filtration and evaporation of the solvent, the crude residual was purified by chromatography on silica gel (dichloromethane/methanol=100/1 (400 mL)) to afford a solid. The resulting solid was recrystallized from ethyl acetate and collected by suction filtration washed with ethyl acetate to afford the product (S,S)-L4 (538.6 mg, 78%) as a solid.

(S,S)-L4: melting point: 143.6-144.4° C. (ethyl acetate). $[\alpha]_D^{20}$=+66.9 (c=0.980, CHCl$_3$); $^1$H NMR (300 MHz, CDCl$_3$) δ 7.41-7.19 (m, 20H, ArH), 7.19-6.99 (m, 10H, ArH), 6.97-6.82 (m, 2H, NH×2), 5.28-5.15 (m, 2H, NCH× 2), 2.33-2.09 (m, 8H, CH$_2$×4); $^{13}$C NMR (75 MHz, CDCl$_3$) δ 173.0 (d, J=13.8 Hz), 138.6, 137.8 (d, J=2.8 Hz), 137.6 (d, J=3.5 Hz), 132.8, 132.7, 132.5, 132.4, 128.71, 128.66, 128.5, 128.43, 128.42, 127.7, 127.4, 59.3, 32.7 (d, J=17.9 Hz), 23.3 (d, J=12.4 Hz); $^{31}$P NMR (121.5 MHz, CDCl$_3$) δ-16.0; IR (KBr) ν (cm$^{-1}$) 3285, 3067, 3050, 3024, 2912, 1642, 1535, 1491, 1478, 1431, 1364, 1250, 1049; MS (EI): m/z (%) 692 ([M]$^+$, 7.23), 346 (100); Anal. Calcd. for C$_{44}$H$_{42}$N$_2$O$_2$P$_2$ (%): C 76.28, H 6.11, N 4.04; Found: C 76.09, H 6.14, N 3.93.

Example (7) 3-methyl-4-benzyl-4-(2-butyl-2,3-butadienyl)-1-phenylpyrazoline-5-one (6aa) (zyc-4-30)

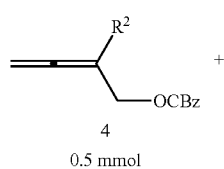

4
0.5 mmol

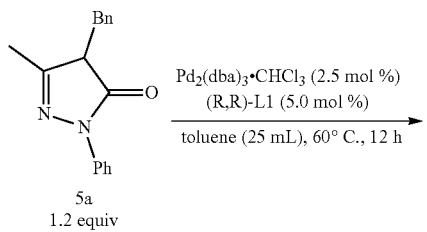

Under a nitrogen environment, tris(dibenzylideneacetone) dipalladium-chloroform adduct (12.9 mg, 0.0125 mmol), (R,R)-L1 (14.3 mg, 0.025 mmol)/toluene (5 mL), 4a (131.5 mg, 0.5 mmol)/toluene (11.7 mL), and 5a (158.7 mg, 0.6 mmol)/toluene (8.3 mL) were added to a dried reaction flask, then stirred at 60° C. for 12 hours. The resulting mixture was filtrated through a short column of silica gel and eluted with ethyl acetate (15 mL×3). After evaporation, the residue was purified by chromatography on silica gel (eluent: petroleum ether (60-90° C.)/ethyl acetate=60/1) to afford a pure part of 6aa and the impure part was further purified by chromatography on silica gel (eluent: petroleum ether (60-90° C.)/ethyl acetate=40/1). Two-round chromatography afforded 6aa (179.5 mg, 96%) as a liquid 6aa: 94.6% ee (HPLC condition: Chiralcel IA column, n-hexane/i-PrOH=90/10, 1.0 mL/min, λ=254 nm, t$_R$ (major)= 5.7 min, t$_R$ (minor)=8.9 min); $[\alpha]_D^{20}$=−8.2 (c=1.250, CHCl$_3$); $^1$H NMR (300 MHz, CDCl$_3$) δ 7.55 (d, J=8.1 Hz, 2H, ArH), 7.30 (t, J=7.8 Hz, 2H, ArH), 7.22-7.02 (m, 6H, ArH), 4.56 (t, J=2.7 Hz, 2H, CH$_2$=C), 3.18 (d, J=13.2 Hz, 1H, one proton of CH$_2$), 2.89 (d, J=13.5 Hz, 1H, one proton of CH$_2$), 2.69 (dt, J$_1$=15.3 Hz, J$_2$=3.3 Hz, 1H, one proton of CH$_2$), 2.39 (d, J=15.0 Hz, 1H, one proton of CH$_2$), 2.14 (s, 3H, CH$_3$), 1.93-1.80 (m, 2H, CH$_2$), 1.43-1.17 (m, 4H, CH$_2$×3), 0.83 (t, J=7.1 Hz, 3H, CH$_3$); $^{13}$C NMR (75 MHz, CDCl$_3$) δ 205.3, 174.6, 161.4, 137.6, 134.1, 129.1, 128.5, 128.1, 127.2, 124.8, 119.3, 98.3, 77.7, 60.1, 42.8, 36.1, 32.3, 29.4, 22.1, 14.7, 13.8; IR (neat) ν (cm$^{-1}$) 3063, 3031, 2956, 2927, 2859, 1954, 1712, 1597, 1500, 1455, 1440, 1402, 1366, 1123; MS (EI): m/z (%) 372 ([M]$^+$, 31.27), 186 (100); HRMS calcd. for C$_{25}$H$_{28}$N$_2$O [M]$^+$: 372.2202; Found: 372.2202.

Example (8) 3-methyl-4-(4-methylbenzyl)-4-(2-butyl-2,3-butadienyl)-1-phenylpyrazoline-5-one (6ab) (zyc-4-75)

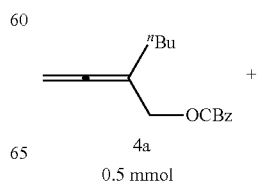

4a
0.5 mmol

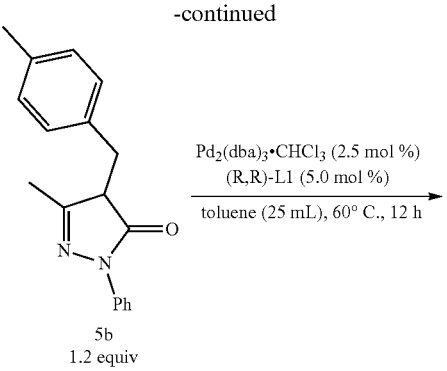

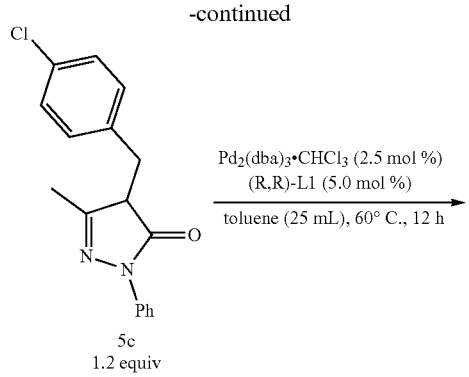

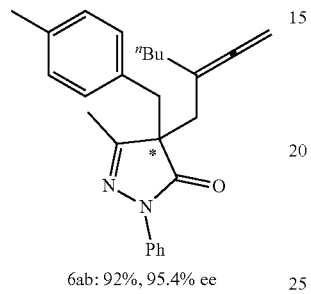

6ab: 92%, 95.4% ee

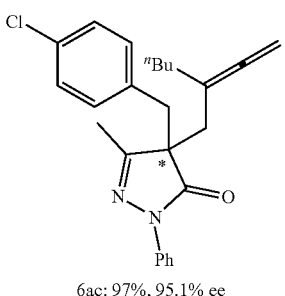

6ac: 97%, 95.1% ee

Operations were conducted by referring to Example (7). Under a nitrogen environment, tris(dibenzylideneacetone) dipalladium-chloroform adduct (12.8 mg, 0.0125 mmol), (R,R)-L1(14.3 mg, 0.025 mmol) and toluene (5 mL), 4a (131.1 mg, 0.5 mmol)/toluene (11.7 mL), 5b (167.0 mg, 0.6 mmol)/toluene (8.3 mL) were added to a dried reaction flask, and stirred at 60° C. for 12 hours to obtain the product 6ab (178.1 mg, 92%) (petroleum ether/diethyl ether=60/1 (600 mL) to 40/1 (1000 mL)) as a liquid.

6ab: 95.4% ee (HPLC condition: Chiralcel IA column, n-hexane/i-PrOH=90/10, 1.0 mL/min, λ=254 nm, $t_R$ (major)= 5.7 min, $t_R$ (minor)=7.9 min); $[α]_D^{20}$=−24.9 (c=1.125, CHCl$_3$); $^1$H NMR (300 MHz, CDCl$_3$) δ 7.60 (d, J=7.5 Hz, 2H, ArH), 7.30 (t, J=8.0 Hz, 2H, ArH), 7.10 (t, J=7.5 Hz, 1H, ArH), 7.00-6.90 (m, 4H, ArH), 4.55 (p, J=3.0 Hz, 2H, CH$_2$=C), 3.14 (d, J=13.2 Hz, 1H, one proton of CH$_2$), 2.84 (d, J=13.5 Hz, 1H, one proton of CH$_2$), 2.68 (dt, $J_1$=15.3 Hz, $J_2$=3.3 Hz, 1H, one proton of CH$_2$), 2.37 (dt, $J_1$=15.3 Hz, $J_2$=2.2 Hz, 1H, one proton of CH$_2$), 2.19 (s, 3H, CH$_3$), 2.12 (s, 3H, CH$_3$), 1.92-1.80 (m, 2H, CH$_2$), 1.40-1.17 (m, 4H, CH$_2$×2), 0.82 (t, J=7.1 Hz, 3H, CH$_3$); $^{13}$C NMR (75 MHz, CDCl$_3$) δ 205.3, 174.7, 161.5, 137.7, 136.7, 131.0, 128.9, 128.8, 128.5, 124.7, 119.2, 98.3, 77.5, 60.1, 42.4, 36.1, 32.3, 29.4, 22.1, 20.9, 14.7, 13.7; IR (neat) ν (cm$^{-1}$) 2956, 2925, 2869, 2856, 1955, 1708, 1597, 1515, 1500, 1457, 1441, 1402, 1365, 1326, 1121; MS (EI): m/z (%) 386 ([M]$^+$, 22.51), 105 (100); HRMS calcd. for C$_{26}$H$_{30}$N$_2$O [M]$^+$: 386.2358; Found: 386.2361.

Example (9) 3-methyl-4-(4-chlorobenzyl)-4-(2-butyl-2,3-butadienyl)-1-phenylpyrazoline-5-one (6ac) (zyc-4-76)

Operations were conducted by referring to Example (7). Under a nitrogen environment, tris(dibenzylideneacetone) dipalladium-chloroform adduct (13.0 mg, 0.0125 mmol), (R,R)-L1(14.4 mg, 0.025 mmol) and toluene (5 mL), 4a (131.0 mg, 0.5 mmol)/toluene (11.7 mL), 5c (179.6 mg, 0.6 mmol)/toluene (8.3 mL) were added to a dried reaction flask, and stirred at 60° C. for 12 hours to obtain the product 6ac (197.0 mg, 97%) (petroleum ether/diethyl ether=40/1) as a liquid.

6ac: 95.1% ee (HPLC condition: Chiralcel IA column, n-hexane/i-PrOH=90/10, 1.0 mL/min, λ=254 nm, $t_R$ (major)= 6.7 min, $t_R$ (minor)=8.7 min); $[α]_D^{20}$=−27.9 (c=0.990, CHCl$_3$); $^1$H NMR (300 MHz, CDCl$_3$) δ 7.58 (d, J=7.8 Hz, 2H, ArH), 7.31 (t, J=8.0 Hz, 2H, ArH), 7.18-7.07 (m, 3H, ArH), 7.00 (d, J=8.4 Hz, 2H, ArH), 4.56 (p, J=2.9 Hz, 2H, CH$_2$=C), 3.13 (d, J=13.5 Hz, 1H, one proton of CH$_2$), 2.84 (d, J=13.2 Hz, 1H, one proton of CH$_2$), 2.67 (dt, $J_1$=15.0 Hz, $J_2$=3.2 Hz, 1H, one proton of CH$_2$), 2.36 (d, J=14.7 Hz, 1H, one proton of CH$_2$), 2.13 (s, 3H, CH$_3$), 1.92-1.79 (m, 2H, CH$_2$), 1.42-1.17 (m, 4H, CH$_2$×2), 0.82 (t, J=7.2 Hz, 3H, CH$_3$); $^{13}$C NMR (75 MHz, CDCl$_3$) δ 205.3, 174.3, 161.1, 137.5, 133.1, 132.6, 130.4, 128.6, 128.3, 124.9, 119.1, 98.1, 77.7, 60.0, 41.9, 36.1, 32.3, 29.3, 22.0, 14.6, 13.7; IR (neat) ν (cm$^{-1}$) 3062, 3046, 2956, 2927, 2871, 2856, 1955, 1709, 1597, 1500, 1458, 1441, 1402, 1366, 1323, 1299, 1245, 1181, 1122, 1097, 1016; MS (EI): m/z (%) 408 ([M(Cl$^{37}$)]$^+$, 15.32), 406 ([M(Cl$^{35}$)]$^+$, 38.40), 125 (100); HRMS calcd. for C$_{25}$H$_{27}$$^{35}$ClN$_2$O [M]$^+$: 406.1812; Found: 406.1814.

Example (10) 3-methyl-4-(α-naphthylmethyl)-4-(2-butyl-2,3-butadienyl)-1-phenylpyrazoline-5-one (6ad) (zyc-4-92)

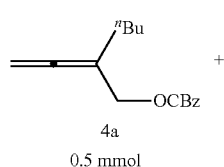

4a
0.5 mmol

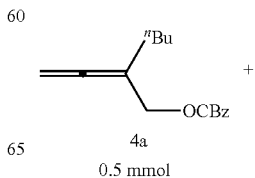

4a
0.5 mmol

-continued

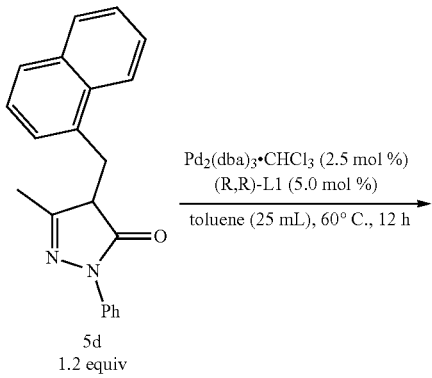

5d
1.2 equiv

Pd₂(dba)₃·CHCl₃ (2.5 mol %)
(R,R)-L1 (5.0 mol %)
———————————————→
toluene (25 mL), 60° C., 12 h 6ad: 95%, 96.7% ee Operations were conducted by referring to Example (7). Under a nitrogen environment, tris(dibenzylideneacetone) dipalladium-chloroform adduct (12.9 mg, 0.0125 mmol), (R,R)-L1(14.3 mg, 0.025 mmol) and toluene (5 mL), 4a (131.1 mg, 0.5 mmol)/toluene (11.7 mL), 5d (188.4 mg, 0.6 mmol)/toluene (8.3 mL) were added to a dried reaction flask, and stirred at 60° C. for 12 hours to obtain the product 6ad (200.9 mg, 95%) (petroleum ether/diethyl ether=50/1) as a liquid.

6ad: 96.7% ee (HPLC condition: Chiralcel IA column, n-hexane/i-PrOH=90/10, 1.0 mL/min, λ=254 nm, $t_R$ (major)= 6.5 min, $t_R$ (minor)=11.1 min); $[α]_D^{20}$=−47.4 (c=1.030, CHCl₃); ¹H NMR (300 MHz, CDCl₃) δ 8.09 (d, J=8.7 Hz, 1H, ArH), 7.76 (d, J=8.1 Hz, 1H, ArH), 7.70-7.62 (m, 1H, ArH), 7.56 (d, J=8.7 Hz, 2H, ArH), 7.52-7.37 (m, 2H, ArH), 7.33-7.22 (m, 4H, ArH), 7.08 (t, J=7.4 Hz, 1H, ArH), 4.53 (p, J=3.0 Hz, 2H, CH₂=C), 3.64 (d, J=14.1 Hz, 1H, one proton of CH₂), 3.41 (d, J=14.4 Hz, 1H, one proton of CH₂), 2.78 (dt, J₁=15.3 Hz, J₂=3.5 Hz, 1H, one proton of CH₂), 2.48 (dt, J₁=14.7 Hz, J₂=2.3 Hz, 1H, one proton of CH₂), 1.98-1.80 (m, 5H, CH₃ and CH₂), 1.42-1.15 (m, 4H, CH₂×2), 0.82 (t, J=7.1 Hz, 3H, CH₃); ¹³C NMR (75 MHz, CDCl₃) δ 205.3, 175.1, 162.0, 137.8, 133.7, 132.0, 130.7, 128.7, 128.5, 128.1, 127.5, 125.8, 125.5, 124.9, 124.7, 123.6, 119.1, 98.3, 77.8, 59.5, 38.1, 36.1, 32.4, 29.4, 22.1, 15.1, 13.8; IR (neat) ν (cm⁻¹) 3062, 3046, 2956, 2927, 2871, 2852, 1954, 1709, 1597, 1500, 1457, 1399, 1365, 1322, 1121; MS (EI): m/z (%) 422 ([M]⁺, 21.84), 186 (100); HRMS calcd. for C₂₉H₃₀N₂O [M]⁺: 422.2358; Found: 422.2361.

Example (11) 3-methyl-4-ethyl-4-(2-butyl-2,3-butadienyl)-1-phenylpyrazoline-5-one (6ae) (zyc-4-64)

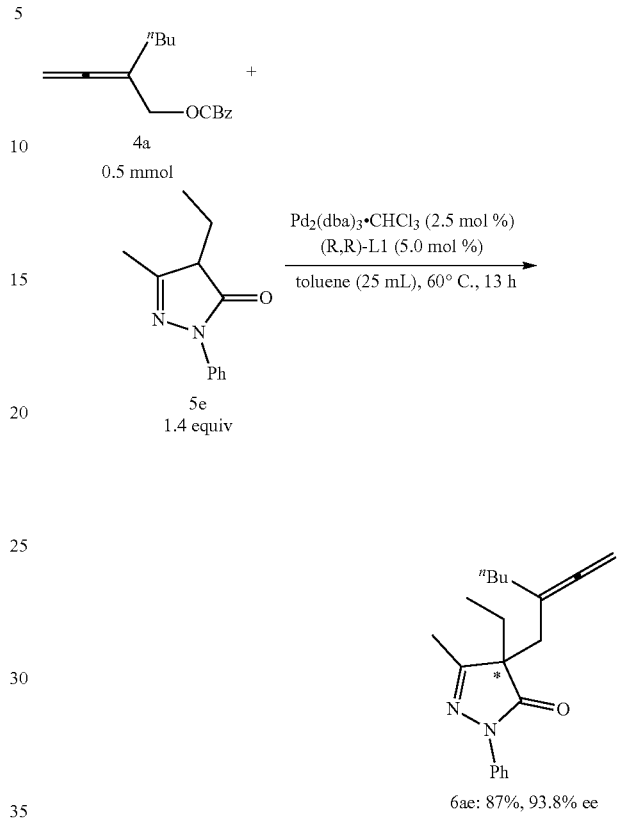

6ae: 87%, 93.8% ee

Operations were conducted by referring to Example (7). Under a nitrogen environment, tris(dibenzylideneacetone) dipalladium-chloroform adduct (12.9 mg, 0.0125 mmol), (R,R)-L1(14.3 mg, 0.025 mmol) and toluene (5 mL), 4a (131.0 mg, 0.5 mmol)/toluene (11.7 mL), 5e (141.6 mg, 0.7 mmol)/toluene (8.3 mL) were added to a dried reaction flask, and stirred at 60° C. for 13 hours to obtain the product 6ae (134.6 mg, 87%) (petroleum ether/diethyl ether=40/1, the impure part was subjected to the column chromatography again, petroleum ether/ethyl acetate=40/1, combined) as a liquid.

6ae: 93.8% ee (HPLC condition: Chiralcel IA column, n-hexane/i-PrOH=95/5, 1.0 mL/min, λ=254 nm, $t_R$ (minor)= 5.3 min, $t_R$ (major)=5.8 min); $[α]_D^{20}$=+152.9 (c=0.990, CHCl₃); ¹H NMR (300 MHz, CDCl₃) δ 7.89 (d, J=7.8 Hz, 2H, ArH), 7.38 (t, J=8.0 Hz, 2H, ArH), 7.15 (t, J=7.4 Hz, 1H, ArH), 4.55 (p, J=3.1 Hz, 2H, CH₂=C=C), 2.55 (dt, J₁=15.0 Hz, J₂=3.3 Hz, 1H, one proton of CH₂), 2.25 (d, J=15.0 Hz, 1H, one proton of CH₂), 2.07 (s, 3H, CH₃), 1.97-1.77 (m, 3H, one proton of CH₂ and CH₂), 1.74-1.58 (m, 1H, one proton of CH₂), 1.40-1.13 (m, 4H, CH₂×2), 0.81 (t, J=7.2 Hz, 3H, CH₃), 0.72 (t, J=7.5 Hz, 3H, CH₃); ¹³C NMR (75 MHz, CDCl₃) δ 205.3, 175.1, 162.3, 138.0, 128.6, 124.6, 118.6, 98.3, 77.3, 59.2, 36.3, 32.2, 29.6, 29.3, 22.0, 13.9, 13.7, 7.9; IR (neat) ν (cm⁻¹) 2960, 2931, 2873, 2856, 1955, 1713, 1619, 1597, 1500, 1458, 1403, 1386, 1365, 1311, 1261, 1136, 1094; MS (EI): m/z (%) 310 ([M]⁺, 29.93), 187 (100); HRMS calcd. for C₂₀H₂₆N₂O [M]⁺: 310.2045; Found: 310.2042.

Example (12) 3-methyl-4-allyl-4-(2-butyl-2,3-butadienyl)-1-phenylpyrazoline-5-one (6af) (zyc-4-87)

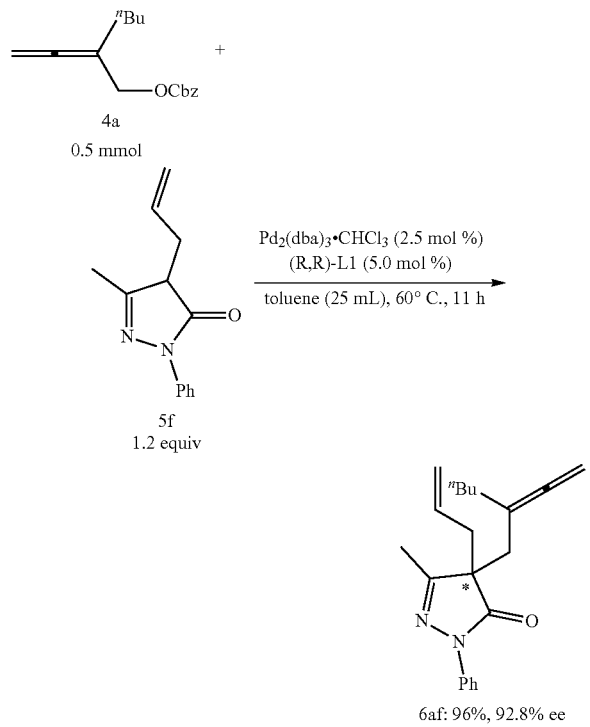

6af: 96%, 92.8% ee

Operations were conducted by referring to Example (7). Under a nitrogen environment, tris(dibenzylideneacetone) dipalladium-chloroform adduct (13.0 mg, 0.0125 mmol), (R,R)-L1(14.2 mg, 0.025 mmol) and toluene (5 mL), 4a (131.5 mg, 0.5 mmol)/toluene (11.7 mL), 5f (128.4 mg, 0.6 mmol)/toluene (8.3 mL) were added to a dried reaction flask, and stirred at 60° C. for 11 hours to obtain the product 6af (155.0 mg, 96%) (petroleum ether/diethyl ether=50/1) as a liquid. 6af: 92.8% ee (HPLC condition: Chiralcel OD column, n-hexane/i-PrOH=98/2, 1.0 mL/min, λ=254 nm, $t_R$ (major)=4.7 min, $t_R$ (minor)=5.2 min); $[α]_D^{20}$=+98.5 (c=0.975, CHCl$_3$); $^1$H NMR (300 MHz, CDCl$_3$) δ 7.87 (d, J=8.1 Hz, 2H, ArH), 7.37 (t, J=8.0 Hz, 2H, ArH), 7.14 (t, J=7.5 Hz, 1H, ArH), 5.57-5.39 (m, 1H, =CH), 5.18-4.96 (m, 2H, =CH$_2$), 4.55 (p, J=2.9 Hz, 2H, CH$_2$=C), 2.65-2.45 (m, 2H, CH$_2$), 2.43-2.20 (m, 2H, CH$_2$), 2.08 (s, 3H, CH$_3$), 1.91-1.73 (m, 2H, CH$_2$), 1.40-1.14 (m, 4H, CH$_2$×2), 0.81 (t, J=6.9 Hz, 3H, CH$_3$); $^{13}$C NMR (75 MHz, CDCl$_3$) δ 205.3, 174.6, 161.8, 137.9, 130.3, 128.6, 124.6, 119.5, 118.7, 98.2, 77.4, 58.4, 40.6, 35.7, 32.2, 29.3, 22.0, 14.2, 13.7; IR (neat) v (cm$^{-1}$) 3079, 3062, 3054, 2956, 2928, 2877, 2859, 1955, 1714, 1642, 1616, 1597, 1500, 1458, 1436, 1402, 1365, 1321, 1243, 1120, 1098, 1031; MS (EI): m/z (%) 322 ([M]$^+$, 41.06), 239 (100); HRMS calcd. for C$_{21}$H$_{26}$N$_2$O [M]$^+$: 322.2045; Found: 322.2044.

What is claimed is:

1. 1,2-bis(diphenylphosphinoalkylamido)-1,2-disubstituted ethane chiral phosphine ligands, wherein, the said 1,2-bis(diphenylphosphinoalkylamido)-1,2-disubstituted ethane has the following structure as formula(I):

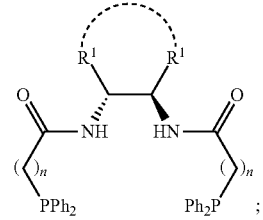

formula (I)

wherein each instance of $R^1$ is selected from the group consisting of a phenyl group, a phenyl group substituted by $C_1$-$C_{10}$ alkyl, a phenyl group substituted by halogen, or an α-naphthyl group;

or alternatively the group represents a —(CH$_2$)$_3$— or —(CH$_2$)$_4$— group;

n=1-6.

2. A method for preparing 1,2-bis(diphenylphosphinoalkylamido)-1,2-disubstituted ethane, which comprises reacting, in an organic solvent, using-1,2-disubstituted-1,2-diaminoethane, diphenylphosphinoacetic acid, p-dimethylaminopyridine and 1-ethyl-(3-dimethylaminopropyl)carbodiimide hydrochloride as reaction raw materials to obtain 1,2-bis(diphenylphosphonylalkylamido)-1,2-disubstituted ethane through an amidation reaction, wherein said reaction has the following reaction equation:

reaction equation (a)

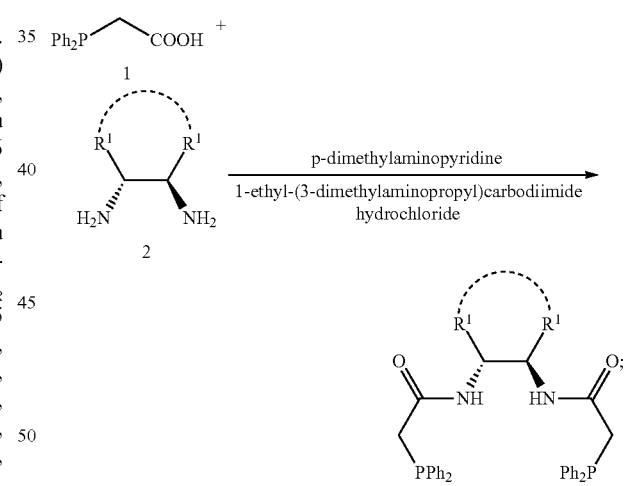

wherein each instance of $R^1$ is selected from the group consisting of a phenyl group, a phenyl group substituted by $C_1$-$C_{10}$ alkyl, a phenyl group substituted by halogen, or an α-naphthyl group;

or alternatively the group represents a —(CH$_2$)$_3$— or —(CH$_2$)$_4$— group.

3. The method of claim 2, wherein, the said organic solvent is dichloromethane; the molar ratio of diphenylphosphinoacetic acid, 1,2-disubstituted-1,2-diaminoethane, p-dimethylaminopyridine and 1-ethyl-(3-dimethylaminopropyl)carbodiimide hydrochloride is (2.1-2.2):1.0:2.1:2.2; and the amidation reaction temperature is 20-30° C.

4. A method for preparing 1,2-bis(diphenylphosphinoalkylamido)-1,2-disubstituted ethane, which comprises reacting in an organic solvent, N-hydroxysuccinimide diphenylphosphonyl alkyl acid ester and 1,2-disubstituted-1,2-diaminoethane as reaction raw materials to obtain the said 1,2-bis(diphenylphosphinoalkylamido)-1,2-disubstituted ethane through an amidation reaction, wherein said reaction has the following reaction equation:

reaction equation (b)

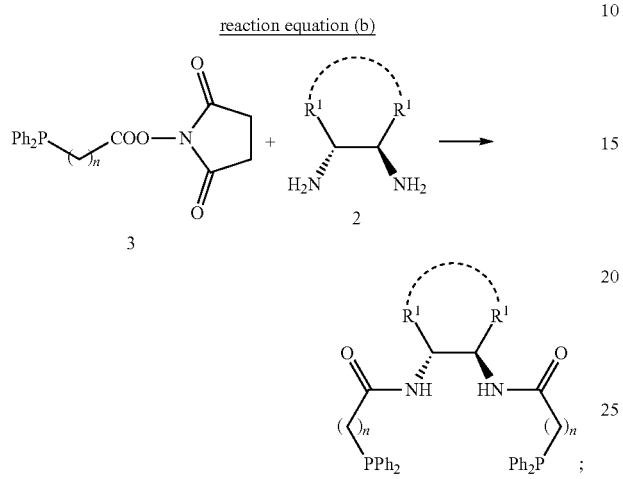

wherein each instance of $R^1$ is selected from the group consisting of a phenyl group, a phenyl group substituted by $C_1$-$C_{10}$ alkyl, a phenyl group substituted by halogen, or an α-naphthyl group;

or alternatively the group $R^1$ $R^1$ represents a —(CH$_2$)$_3$— or —(CH$_2$)$_4$— group; n=1-6.

5. The method of claim 4, wherein, the said organic solvent is dichloromethane; the molar ratio of diphenylphosphinoalkyl acid N-hydroxysuccinimide ester and 1,2-disubstituted-1,2-diaminoethane is (2.1-2.2):1.0; and the amidation reaction temperature is 20-30° C.

6. A method of preparing a chiral 3-methyl-4-benzyl-4-(2-butyl-2,3-butadienyl)pyrazoline-5-one, which comprises using the 1,2-bis(diphenylphosphinoalkylamido)-1,2-disubstituted ethane according to claim 1 in an enantioselective reaction.

7. The method of claim 6, which comprises reacting in an organic solvent, tris(dibenzylideneacetone)dipalladium-chloroform adduct, 1,2-bis(diphenylphosphinoalkylamido)-1,2-disubstituted ethane, benzyl(2-alkyl- 2,3-butadienyl) carbonate and 3-methyl-4-benzyl-pyrazoline-5-one as reaction raw materials to obtain the said chiral 3-methyl-4-benzyl-4-(2-butyl-2,3-butadienyl)pyrazoline-5-one,
wherein said reaction has the following reaction equation:

reaction equation (c)

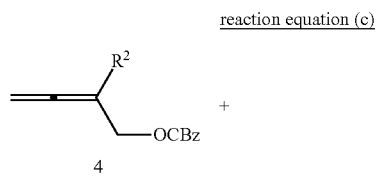

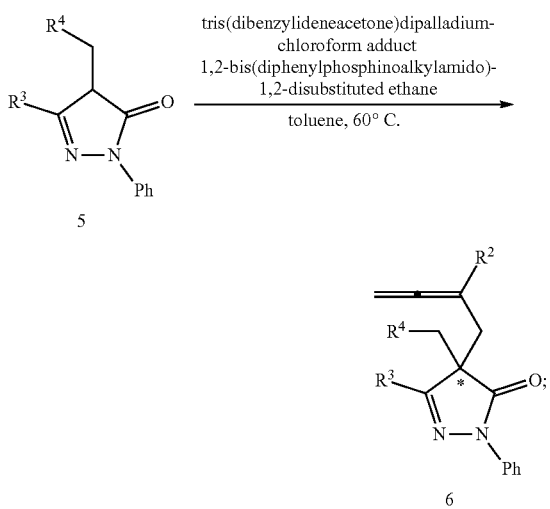

wherein, $R^2$ is C1-C10 alkyl group; $R^3$ is C1-C10 alkyl group;

$R^4$ is phenyl group substituted by halogen, phenyl group substituted by C1-C10 alkyl, benzyl group, α-naphthyl group, C1-C10 alkyl group, alkenyl group.

8. The method of claim 7, wherein, the said organic solvent is of toluene; the said reaction temperature is 30-60° C.

9. The method of claim 7, wherein the molar ratio of benzyl (2-alkyl-2,3-butadienyl) carbonate and 3-methyl-4-benzyl-pyrazoline-5-one is 1.0:(1.2-1.4); the molar ratio of benzyl (2-alkyl-2,3-butadienyl) carbonate and organic solvent is 0.02-0.1 mmol/mL.

10. Chiral 3-methyl-4-benzyl-4-(2-alkyl-2,3-butadienyl) pyrazoline-5-one compounds, wherein, the said chiral 3-methyl-4-benzyl-4-(2-alkyl-2,3-butadienyl)pyrazoline-5-one compounds have the following structure as formula(6):
Wherein, formula (6)

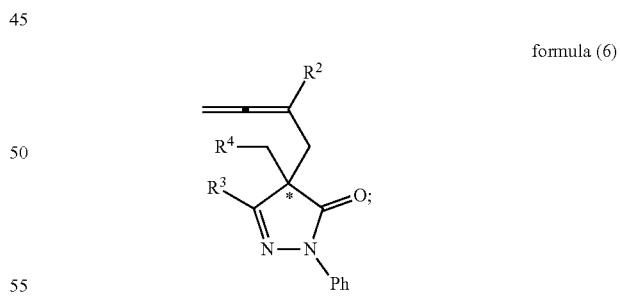

$R^2$ is C1-C10 alkyl group; $R^3$ is $C_1$-$C_{10}$ alkyl group; $R^4$ is phenyl group substituted by halogen, phenyl group substituted by C1-C10 alkyl group, benzyl group, α-naphthyl group, C1-C10 alkyl group, alkenyl group.

* * * * *